United States Patent [19]

Springer et al.

[11] 4,021,556

[45] May 3, 1977

[54] XANTHINE OXIDASE INHIBITORS

[75] Inventors: Robert H. Springer, Santa Ana; Darrell E. O'Brien, Mission Viejo; Lionel N. Simon, Santa Ana, all of Calif.

[73] Assignee: ICN Pharmaceuticals, Inc., Irvine, Calif.

[22] Filed: Nov. 17, 1975

[21] Appl. No.: 632,809

Related U.S. Application Data

[60] Division of Ser. No. 261,103, June 8, 1972, Pat. No. 3,920,652, which is a continuation-in-part of Ser. No. 172,195, Aug. 16, 1971, abandoned.

[52] U.S. Cl. .............................................. 424/251
[51] Int. Cl.² ...................................... A61K 31/505
[58] Field of Search ................................... 424/251

[56] References Cited

UNITED STATES PATENTS

| | | | |
|---|---|---|---|
| 3,048,587 | 8/1962 | Oroshnik | 260/256.4 |
| 3,296,268 | 1/1967 | Papesch | 260/256.4 |

OTHER PUBLICATIONS

Dashkevich et al., Chemical Abstracts, 77:5401f, (1972).
Cutting, Handbook of Pharmacology, 4th Edition, (1969), pp. 248-249.

*Primary Examiner*—Norman A. Drezin
*Attorney, Agent, or Firm*—Kay H. Boswell

[57] ABSTRACT

Compounds of the following structure are disclosed which are effective inhibitors of the enzyme xanthine oxidase:

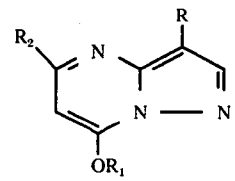

R is an aromatic or substituted aromatic nucleus such as phenyl, $R_1$ is H, an alkali metal or ammonium, and $R_2$ is H or $OR_1$.

6 Claims, No Drawings

XANTHINE OXIDASE INHIBITORS

CROSS REFERENCE TO RELATED APPLICATIONS

This application is a division of application Ser. No. 261,103 filed June 8, 1972, now U.S. Pat. No. 3,920,652 which in turn was a continuation-in-part of application Ser. No. 172,195 filed Aug. 16, 1971, now abandoned.

BACKGROUND OF THE INVENTION

It is now well established that the enzyme xanthine oxidase is implicated in the production of uric acid by the body, converting hypoxanthine into xanthine and xanthine, in turn, into uric acid. Under normal conditions, uric acid (2,6,8-trioxypurine) is found in the body in only small amounts, a concentration in the blood on the order of about one to about three micrograms per 100 milliliters. Under certain pathological conditions, however, as for example, gout, the concentration of uric acid increases significantly.

Gout, of course, is a metabolic disturbance in the body resulting from an overproduction of uric acid, chronic hyperuricemia (elevated blood uric acid), and progressive accumulation of uric acid in the tissues. The body may also progressively lose its capacity to excrete uric acid and is, therefore, in a constant state of uric acid imbalance, accumulating a greater and greater excess. Its concentration in the blood is high, and, because of its low solubility, it tends to precipitate and form deposits at various sites where the blood flow is least active, particularly joints and cartilaginous tissues.

One approach to the control of gout commonly used in the past has been the prescription of drugs which tended to prevent the accumulation of uric acid in the body and thus diminish the likelihood of acute recurrences. Such drugs are identified as "uricosuric agents" and promote the excretion of uric acid in the urine. Examples of such drugs include p-dipropylsulfamyl benzoic acid and sulfinpyrazone. These drugs cannot, however, be administered in conjunction with aspirin or any other salicylate, which might be given to relieve pain, because the agents and salicylates are mutually antagonistic, i.e., each tends to offset the action of the other.

A second approach to the treatment of gout which has become popular is the use of the drug allopurinol,

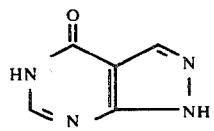

which blocks the production of uric acid by the body by inhibiting the enzyme xanthine oxidase, which, as noted previously, is responsible for converting hypoxanthine into xanthine and xanthine into uric acid. While allopurinol is effective to inhibit the enzyme xanthine oxidase, nevertheless there are disadvantages which limit its suitability.

First, its toxicity is higher than desirable, having a lethal dosage level, $LD_{50}$ (the dose required to kill 50% of a group of animals in two weeks when injected into the intraparietal cavity) of about 150 milligrams per kilogram of body weight. Moreover, allopurinol is gradually metabolized in vivo to 4,6-dihydroxy pyrazolo[3,4-d]pyrimidine, which is not as effective an inhibitor as is allopurinol. In addition to the foregoing disadvantages, allopurinol, because of its chemical nature, must compete with xanthine to occupy a place on the enzyme xanthine oxidase in order to inhibit the enzyme and thus prevent the formation of uric acid by the body, which likewise limits its efficiency. It is also known that acute attacks of gouty arthritis occur in the early treatment with allopurinol. It is accordingly necessary to give colchicine during the initial period of therapy to prevent such acute attacks. There have also been reports of the development of a pruritic rash in some patients and of the occasional occurrence of drowsiness when allopurinol is administered. In view of the foregoing, it is apparent that xanthine oxidase inhibitors which are of acceptable toxicity and at the same time possess increased inhibition efficiency as compared to allopurinol are highly desirable.

In the application of Darrell E. O'Brien and Roland K. Robins entitled "Xanthine Oxidase Inhibitors", Ser. No. 172,196, assigned to the same assignee as this application, imidazo[1,2,a] and pyrazolo[1,5,a]pyrimidine compounds are disclosed which demonstrate significant inhibitory activity. Certain of such compounds possess greater inhibition against the enzyme xanthine oxidase than does allopurinol. While such compounds are thus effective inhibitors, there is yet the need for inhibitors possessing still increased efficiency.

SUMMARY OF THE INVENTION

The present invention thus relates to xanthine oxidase inhibitors comprising pyrazolo[1,5a]pyrimidine compounds of the following general structure:

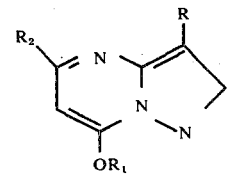

R is an aromatic or substituted aromatic nucleus, as for example, phenyl, naphthyl, tolyl, halogenated phenyls, heterocyclicnuclei, etc., $R_1$ is H, an alkali metal or ammonium, and $R_2$ is H or $OR_1$.

DETAILED DESCRIPTION OF THE INVENTION

The xanthine oxidase inhibitors of this invention are represented by the foregoing structure. As will be seen from the illustrative examples which follow, such compounds demonstrate inhibitory activity significantly greater than allopurinol, in some cases on the order of 100 to 200 times greater.

The R substituent, as indicated previously, is an aromatic or substituted aromatic nucleus. Examples of such substituents include phenyl, 1-naphthyl, substituted phenyls of the formula

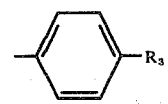

where $R_3$ is $CH_3$, a halogen, or

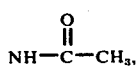

m-tolyl, heterocyclicnuclei as for example

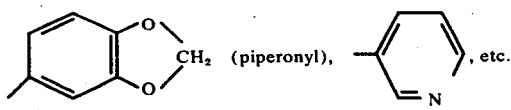

$R_1$ is preferably II thus yielding 5,7-dihydroxy pyrazolo[1,5a]pyrimidines when $R_2$ is $OR_1$, although physiologically acceptable salts as for example, alkali metal or ammonium, may also be used.

The method of preparing the compounds of the present invention is described in detail in the examples which follow. In general, the synthesis method is as follows.

Following the general procedure of E. L. Anderson, J. E. Casey, Jr., L. C. Greene, J. J. Lafferty, and H. E. Reiff (J. Med. Chem., I, 259 (1964)), 3-amino-4-aryl pyrazoles (III) are prepared from aryl acetonitrile derivatives (I).

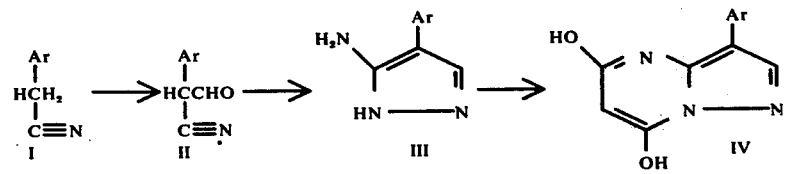

The condensation of such 3-amino-4-aryl pyrazoles (III) with diethyl malonate in the presence of sodium ethoxide solution affords the disodium salts of 3-aryl-5,7-dihydroxypyrazolo[1,5a]pyrimidine. When these sodium salts are dissolved in water and treated with dilute hydrochloric acid, 3-aryl-5,7-dihydroxypyrazolo[1,5a]pyrimidines, represented by (IV), are obtained. It will, of course, be understood that aryl in the foregoing general reaction scheme represents the various aromatic and substituted aromatic nuclei of the compounds of this invention.

Similarly, the condensation of such 3-amino-4-aryl pyrazoles (III) with the sodium salt of ethyl-formylacetate (malonaldehydic ester) in anhydrous ethanol affords the sodium salt of various 3-aryl-7-hydroxypyrazolo[1,5a]pyrimidines. When these sodium salts are dissolved in water and precipitated by the addition of hydrochloric acid, 3-aryl-7-hydroxypyrazolo[1,5a]pyrimidines, represented by (V), are obtained.

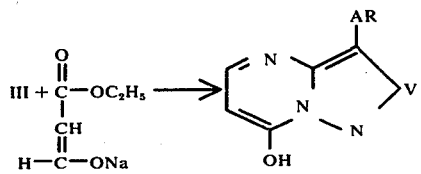

An alternative procedure that is employed for the preparation of these derivatives involves the condensation of the various 3-amino-4-arylpyrazoles (III) with diethyl ethoxymethylene malonate in acetic acid solution to afford various 3-aryl-6-carbethoxy-7-hydroxypyrazolo[1,5a]pyramidines (VI). Refluxing a solution of these 3-aryl-6-carbethoxy-7-hydroxypyrazolo[1,5a]pyrimidines (VI) in 40% sulfuric acid affords the corresponding 3-aryl-7-hydroxypyrazolo[1,5a]pyrimidines (V).

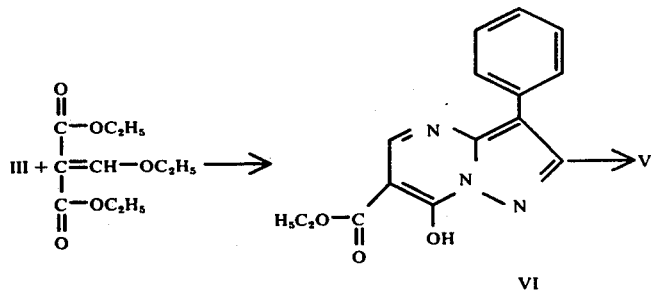

The invention will be better understood by reference to the following specific but illustrative examples. Ultraviolet spectra were recorded on a Cary-15 spectrophotometer.

EXAMPLE I

Preparation of 3-phenyl pyrazolo[1,5,a]pyrimidine-5,7-diol

A solution of sodium ethoxide was prepared by dissolving sodium [1.7g (0.074 formula weights)] in 200 ml of absolute ethanol. Diethylmalonate [6.8g, 42.5 mmoles] and 3-amino-4-phenyl pyrazolo [6.0g, 37.7 mmoles] were added to the sodium ethoxide solution. The resultant solution was stirred and heated at reflux temperature for 16 hours. The mixture was then allowed to cool to room temperature and the sodium salt of the product collected by filtration. The sodium salt was washed well with ethanol, air dried, and then dissolved in 150 ml of water. Acidification of this solution with 6N hydrochloric acid until a pH of 1–2 was obtained afforded the product. The product was separated by filtration, washed with water, and dried at 100°. Reprecipitation of this product from dilute sodium hydroxide solution by the addition of 6N hydrochloric acid afforded 4.03g (48%) of analytically pure product; mp 315-7° (dec); λ max (pH1) 203 (ε 23,400) and 238 (ε 18,200); λ max (pH11) 234 nm (ε 19,500) and 297 nm (ε 16,600).

Anal. calcd. for $C_{12}H_9N_3O_2$: C, 63.4; H, 3.94; N, 18.5. Found: C, 63.2; H, 4.01; N, 18.6.

EXAMPLE II

Preparation of 3-(m-tolyl)pyrazolo[1,5,a]pyrimidine-5,7-diol

A solution of sodium ethoxide was prepared by dissolving sodium [1.6g (0.0695 formula weights)] in 200 ml of absolute ethanol. Diethylmalonate [6.2g, 38.7 mmoles] and 3-amino-4-(m-tolyl) pyrazole [6.0g, 34.7 mmoles] were added to the sodium ethoxide solution. The resultant solution was stirred and slowly warmed to reflux temperature. After reflux was obtained, the white sodium salt of the product began to precipitate. The reflux and stirring were continued for 16 hours and then the mixture was allowed to cool to room temperature. The sodium salt was separated by filtration, washed with absolute ethanol 3(200 ml) and air dried. The sodium salt was then dissolved in 300 ml of water, and the product precipitated from the solution by the addition of 6N hydrochloric acid until a pH of 1-2 was obtained. The product was thoroughly washed with water and dried at 100°. Purification was accomplished by dissolving the product in dilute sodium hydroxide solution and reprecipitating with 6N hydrochloric acid. The product after purification weighed 2.93g (35%) and had a melting point of 284°-5° (du); λ max (pH1) 207 nm (29,200) and 240 nm (ε 20,500); ε max (pH11) 230 nm (26,400) and 286 nm (ε 18,800).

Anal. calcd. for $C_{13}H_{11}N_3O_2$: C, 64.8; H, 4.57; N, 17.4. Found: C, 64.9; H, 4.66; N, 17.4.

EXAMPLE III

Preparation of 3-(p-tolyl)pyrazolo[1,5,a]pyrimidine-5,7-diol

A solution of sodium ethoxide was prepared by dissolving sodium [2.13g (0.092 formula weights)] in 200 ml of absolute ethanol. Diethylmalonate [8.2g, 51 mmoles] and 3-amino-4-(p-tolyl)pyrazole[8.0g, 46.2 mmoles] were added to the sodium ethoxide solution. The resultant solution was stirred and slowly warmed to reflux temperature. After reflux was obtained, the white sodium salt of the product began to precipitate. The reflux and stirring were continued for 6 hours and then the mixture was allowed to cool to room temperature. The sodium salt was separated by filtration, washed with absolute ethanol, air dried, and then dissolved in 300 ml of water. Acidification of this solution with 6N hydrochloric acid until a pH of 1-2 was obtained afforded the product. The product was separated by filtration, washed with water, dried at 100°, and purified by reprecipitating from sodium hydroxide solution by the addition of 6N hydrochloric acid. The product after purification weighed 4.55g (41%) and had a melting point of 255°-7° (dec); λ max (pH1) 203 nm (ε 30,600) and 243 nm (ε 20,500).

Anal. calcd. for $C_{13}H_{11}N_3O_2$: C, 64.8; H, 4.57; N, 17.4 Found: C, 64.9; H, 4.51; N, 17.3

EXAMPLE IV

Preparation of 3-(p-bromophenyl)pyrazolo[1,5,a]pyramidine-5,7-diol

A solution of sodium ethoxide was prepared by dissolving sodium [0.97g (0.042 formula weights)] in 100 ml of absolute ethanol. Diethylmalonate [0.7g, 23 mmoles] and 3-amino-4-(p-bromophenyl)-pyrazole[5.0g, 21 mmoles] were added to the sodium ethoxide solution. The resultant solution was stirred and slowly warmed to reflux temperature. After reflux was obtained, the white sodium salt of the product began to precipitate from the solution. The reflux and stirring were continued for 6 hours, and then the mixture was allowed to cool to room temperature. The sodium salt was separated by filtration, washed with absolute ethanol, air dried, and dissolved in 100 ml of water. The product was precipitated from this solution by the addition of 6N hydrochloric acid until a pH of 1-2 was obtained. The product was separated by filtration, washed with water, dried at 100°, and purified by reprecipitating from sodium hydroxide solution by the addition of 6N hydrochloric acid. The product after purification weighed 2.31g (36%) and had a melting point of 330°-2° (dec); λ max (pH1) 202 nm (ε 31,900) and 247 nm (ε 27,500); λ max (pH11) 234 nm (68 41,400) and 308 nm (ε 37,100).

Anal. Calcd. for $C_{12}H_8BrN_3O_2$: C, 47.1; H, 2.62; N, 13.7 Found: C, 47.2; H, 2.58; N, 13.8.

EXAMPLE V

Preparation of 3-(p-chlorophenyl)pyrazolo[1,5,a]pyrimidine-5,7-diol

A solution of sodium ethoxide was prepared by dissolving sodium [0.356g (0.0155 formula weights)] in 100 ml of absolute ethanol. Diethylmalonate [1.38g, 8.6 mmoles] were added to the sodium ethoxide solution. The resultant solution as stirred and slowly warmed to reflux temperature. After reflux was obtained, the white sodium salt of the product began to precipitate from the solution. The reflux and stirring were continued for 6 hours, and then the mixture was allowed to cool to room temperature. The sodium salt was separated by filtration, washed with absolute ethanol, air dried, and dissolved in 100 ml of water. The product was precipitated from this solution by the addition of 6N hydrochloric acid until a pH of 1-2 was obtained. The product was separated by filtration, washed with water, dried at 100°, and purified by reprecipitating from sodium hydroxide solution by the addition of 6N hydrochloric acid. The product after purification weighed 1.16g (57%) and had a melting point of 330°-1° (dec); λ max (pH1) 204 nm (ε 26,500) and 245 nm (ε 23,700); λ max (pH11) 233 nm (ε 24,000) and 305 nm (ε 21,500).

Anal. calcd. for $C_{12}H_8ClN_3O_2$: C, 55.1; H, 3.06; N, 6.1 Found: C, 55.1; H, 3.06; N, 16.2.

EXAMPLE VI

Preparation of 3-(p-acetamidophenyl)pyrazolo[1,5,a]pyrimidine-5,7-diol

A solution of sodium ethoxide was prepared by dissolving sodium [1.06g (0.046 formula weights)] in 200 ml of absolute ethanol. Diethylmalonate [4.2g, 26 mmoles] were added to the sodium ethoxide solution.

The resultant solution was stirred and heated at reflux temperature for 16 hours. The mixture was then allowed to cool to room temperature and the sodium salt of the product collected by filtration. The sodium salt was washed well with ethanol, air dried, and then dissolved in 150 ml of water. Acidification of this solution with 6N hydrochloric acid until a pH of 1–2 was obtained afforded the product. The product was separated by filtration, washed with water, and dried at 100°. Reprecipitation of this product from dilute sodium hydroxide solution by the addition of 6N hydrochloric acid afforded 3.54g (54%) of analytically pure product; 272°–4° (dec); λ max (pH1) 204 nm ($\epsilon$ 38,500) and 262 nm ($\epsilon$ 31,100); λ max (pH11) 232 nm ($\epsilon$ 36,000) and 311 nm ($\epsilon$ 32,000).

Anal. calcd. for $C_{14}H_{12}N_4O_3 \cdot 2H_2O$; C, 52.4; H, 5.03; N, 17.5. Found: C, 52.5; H, 5.10; N, 17.8.

EXAMPLE VII

Preparation of 3-piperonylpyrazolo[1,5,a]pyrimidine-5,7-diol

A solution of sodium ethoxide was prepared by dissolving sodium [1.78g (0.077 formula weights 0] in 200 ml of absolute ethanol. Diethylmalonate [3.21g, 20 mmoles] and 3-amino-4-piperonylpyrazole[3.65g, 17.9 mmoles] were added to the sodium ethoxide solution. The resultant solution was stirred and heated at reflux temperature for 16 hours. The mixture was then allowed to cool to room temperature and the sodium salt was washed well with ethanol, air dried, and then dissolved in 150 ml of water. Acidification of this solution with 6N hydrochloric acid until a pH of 1–2 was obtained afforded the product. The product was separated by filtration, washed with water, and dried at 100°. Reprecipitation of this product from dilute sodium hydroxide solution by the addition of 6N hydrochloric acid afforded 3.25g (59%) of analytically pure product; 245°–6° (dec); λ max (pH1) 305 nm ($\epsilon$ 29,950), 257 nm (sh) ($\epsilon$ 13,300) and 295 nm ($\epsilon$ 10,450), λ max (pH11) 230 nm ($\epsilon$ 17,300) and 275 nm ($\epsilon$ 14,100).

Anal. calcd. for $C_{13}H_9N_3O_4$: C, 57.6; N, 3.34; N, 15.5. Found: C, 57.3; H, 3.62; N, 15.5.

EXAMPLE VIII

Preparation of 3-(3'-pyridyl)pyrazolo[1,5,a]pyrimidine-5,7-diol

A solution of sodium ethoxide was prepared by dissolving sodium [2.76g (0.12 formula weights)] in 200 ml of absolute ethanol. Diethylmalonate [10.55g, 66 mmoles] and 3-amino-4-(3'-pyridyl)pyrazole[9.60g, 60 mmoles] were added to the sodium ethoxide solution. The resultant solution was stirred and slowly warmed to reflux temperature. After reflux was obtained, the sodium salt of the product began to precipitate. The reflux and stirring were continued for 16 hours and then the mixture was allowed to cool to room temperature. The sodium salt was separated by filtration, washed with absolute ethanol 3(200 ml) and air dried. The sodium salt was then dissolved in 300 ml of water, and the product precipitated from the solution by the addition of 6N hydrochloric acid until a pH of 1–2 was obtained. The product was separated by filtration, washed with water, and dried at 100°. Purification was accomplished by dissolving the product in dilute sodium hydroxide solution and reprecipitating with 6N hydrochloric acid. The product after purification weighed 3.52g (25%) and had a melting point of 275°–7° (dec); λ max (pH1) 205 nm (sh) ($\epsilon$ 27,450), 215 nm ($\epsilon$ 28,500), 242 nm ($\epsilon$ 20,500) and 280 nm ($\epsilon$ 19,500); λ max (pH11) 232 nm ($\epsilon$ 31,750) and 275 nm, ($\epsilon$ 25,000).

Anal. calcd. for $C_{11}H_8N_4O_2$: C, 57.9; H, 3.53; N, 24.6. Found: C, 57.5; H, 3.42; N, 24.9

EXAMPLE IX

Preparation of 3-(1'-naphthyl)pyrazolo[1,5,a]pyrimidine-5,7-diol

A solution of sodium ethoxide was prepared by dissolving sodium [1.38g (0.06 formula weights 0] in 200 ml of absolute ethanol. Diethylmalonate [5.27g, 33 mmoles] and 3-amino-4-(1'-naphthyl)pyrazole [6.26g, 30 mmoles] were added to the sodium ethoxide solution. The resultant solution was stirred and heated at reflux temperature for 16 hours. The mixture was then allowed to cool to room temperature and the sodium salt of the product collected by filtration. The sodium salt was washed well with ethanol, air dried, and then dissolved in 150 ml of water. Acidification of this solution with 6N hydrochloric acid until a pH of 1–2 was obtained afforded the product. The product was separated by filtration, washed with water and dried at 100°. Reprecipitation of this product from dilute sodium hydroxide solution by the addition of 6N hydrochloric acid afforded 1.91g (23%) of analytically pure product; 219°–21° (dec); λ max (pH1) 205 nm ($\epsilon$ 32,500) 256 nm ($\epsilon$ 15,700) and 290 nm ($\epsilon$ 12,100); λ max (pH11) 230 nm ($\epsilon$ 19,400) and 275 nm ($\epsilon$ 15,700).

Anal. calcd. for $C_{16}H_{11}N_3O_2$: C, 69.3; H, 4.00; N, 15.2. Found: C, 68.5; H, 3.72; N, 14.9.

EXAMPLE X

Preparation of 3-(m-tolyl)pyrazolo[1,5a]pyrimidin-7-ol

A suspension of sodium metal [4.0 g, 0.174 formula weights] in absolute ether (1 liter) was stirred at room temperature while a mixture of ethyl formate [14.8 g, 0.2 moles] and ethyl acetate [17 g, 0.193 moles] was added dropwise. The resultant mixture was stirred at room temperature for 48 hours, at which time all of the sodium metal had reacted. The mixture was evaporated to dryness at reduced pressure and the residue of crude ethyl α-formylacetate was dissolved in absolute ethanol (500 ml). This solution was stirred at room temperature while 3-amino-4-(m-tolyl)pyrazole [10.0 g, 0.0625 moles] was added. This mixture was then heated at reflux for 4 hours and then evaporated to dryness. The solid residue was dissolved in 200 ml of water, treated with decolorizing carbon, and filtered. Acidification of the filtrate with concentrated hydrochloric acid afforded 8.3 g (59%) of 3-(m-tolyl)pyrazolo[1,5a]pyrimidin-7-ol that had a melting point of 308°–10° (dec).

Reprecipitation of this product from dilute sodium hydroxide solution did not change the melting point. λ Max (pH1) at 206 nm ($\epsilon$ 24,600) and 272 nm ($\epsilon$ 13,080). λ Max (pH11) at 226 nm ($\epsilon$ 9,700) and 327 nm ($\epsilon$ 12,870); shoulder in pH 11 at 293 nm.

Anal. Calcd for $C_{13}H_{11}N_3O$: C, 69.5; H, 4.90; N, 18.7. Found: C, 69.5; H, 5.09; N, 18.5.

EXAMPLE XI

Preparation of 3-(m-tolyl)pyrazolo[1,5a]pyrimidin-7-ol

A suspension of sodium metal [4.0 g, 0.174 formula weights] in absolute ether (1 liter) was stirred at room temperature while a mixture of ethyl formate [14.8 g, 0.2 moles] and ethyl acetate [17 g, 0.193 moles] was added dropwise. The resultant mixture was stirred at room temperature for 48 hours, at which time all of the sodium metal had reacted. The mixture was evaporated to dryness at reduced pressure and the residue of crude ethyl α-formylacetate was dissolved in absolute ethanol (500 ml). This solution was stirred at room temperature while 3-amino-4-phenylpyrazole [10.0 g, 0.063 moles] was used. This mixture was then heated at reflux for 4 hours and then evaporated to dryness. The solid residue was dissolved in 200 ml of water, treated with decolorizing carbon, and filtered. Acidification of the filtrate with concentrated hydrochloric acid afforded 9.6 g (69%) of 3-phenylpyrazolo[1,5a]pyrimidine-7-ol that had a melting point of 322°-4° (dec). λ Max (pH 1) at 208 nm (ε 26,800) and 273 nm (ε 12,150). λ Max (pH 11) at 225 nm (ε 11,000) and 329 nm (ε, 7,400); shoulder in pH 11 at 294 nm.

Anal. Calc'd for $C_{12}H_9N_3O$: C, 68.3, H, 4.26, N, 19.9 Found: C, 68.1, H, 4.25, N, 20.2

EXAMPLE XII

Preparation of 6-carbethoxy-3-(m-tolyl)pyrazolo[1,5a]-pyrimidin-7-ol

A solution of 3-amino-4-m-tolylpyrazole [18.3 g, 0.1 mole] and diethyl ethoxymethylenemalonate [21.6 g. 0.1 mole] in 200 ml of acetic acid was stirred and heated at reflux for 3 hours. A complete solution was formed initially; however, after refluxing for about 1½ hours the product began to precipitate from the boiling solution. The mixture was allowed to cool to room temperature, and the product was separated by filtration, washed with methanol, and dried. Recrystallization from a mixture of dimethylformamide and water afforded 18.6 g (63%) of analytically pure 6-carbethoxy 3-(m-tolyl)pyrazolo[1,5a]pyrimidin-7-ol that had a melting point of 278°-80° (dec). λ Max (pH 1) 211 nm (ε 32,700) and 292 nm (ε 13,660). λ Max (pH 11) 227 nm (ε 17,800) and 319 nm (ε, 22,300).

Anal. calc'd for $C_{16}H_{15}N_3O_3$: C, 64.6; H, 5.05; N, 14.12. Found: C, 64.53; H, 5.09; N, 14.11.

EXAMPLE XIII

Preparation of 3-(m-tolyl)pyrazolo[1,5a]pyrimidin-7-ol

A suspension of 6-carbethoxy-3-(m-tolyl)-pyrazolo[1,5a]pyrimidin-7-ol (1 g) in 5 ml of 40% sulfuric acid was stirred and heated at reflux for 2½ hours. At the end of this time, the solution was cooled and added to 10 ml of water. Aqueous sodium hydroxide solution was added to this suspension until a pH of 4 was obtained. The white product was separated by filtration, washed with water, and then recrystallized from a mixture of dimethylformamide and water to afford analytically pure 3-(m-tolyl)pyrazolo[1,5a]-pyrimidin-7-ol that is identical in all respects to the product obtained in Example XI.

EXAMPLE XIV

In this example, the inhibitory activity of the compounds of the invention was determined by recording spectral changes at a constant wavelength of 290 nm, using a Cary Model 15 recording spectrophotometer equipped with a 0–0.1 O.D. slidewire. To facilitate dissolution in the incubation mixture, the compounds of this invention were dissolved in DMSO (pure spectral grade); which is a good solvent and also one which does not inhibit the enzyme. After dissolving in DMSO, the compounds were introduced into the incubation mixture containing 150 micromoles of tris HCl buffer (pH 7.50), 0.6 micromoles EDTA, 0.013 micromoles xanthine, and 20 to 40 micrograms of xanthine oxidase in a final volume of 3.0 milliliters. The xanthine oxidase was purified milk xanthine oxidase from Worthington Biochemical Corporation and had a specific activity of 0.29 u/mg of protein. The assay was carried out by mixing all the components in a cuvette at 25° C. The reaction was started by the addition of the enzyme with the aid of a stirrer-adder. Changes in O.D. were measured for several minutes, and the rate (O.D. per minute) was calculated from the spectral change over the first 15 seconds.

In order to fully evaluate the inhibitory activity and to compare the relative inhibitory abilities of the compounds of this invention with allopurinol, experiments were carried out in which the concentration of inhibitor was varied over a range of approximately $10^{-4}$ to about $10^{-8}$ molar and the initial velocity of xanthine oxidation was measured. From a plot of the log of inhibitor concentration against the percent inhibition, the concentration of inhibitor giving 50% inhibition ($I_{50}$) was calculated. This value was obtained from a linear regression analysis of the straight lines obtained in this graph. The data is presented in Table I as ($I_{50}$) values, and relative activity (α) of the particular compounds of the invention compared to allopurinol is also presented.

TABLE I

| Compound R | $R_1$ | $R_2$ | $I_{50}$ | $\alpha = \dfrac{I_{50}\text{ Allopurinol}}{I_{50}\text{ Compound}}$ |
|---|---|---|---|---|
| 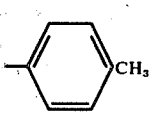 | H | OH | $9.6 \times 10^{-8}$ | 52 |

TABLE I-continued

| Compound R | $R_1$ | $R_2$ | $I_{50}$ | $\alpha = \dfrac{I_{50}\ \text{Allopurinol}}{I_{50}\ \text{Compound}}$ |
|---|---|---|---|---|
| 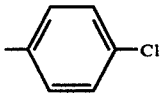 | H | OH | $4.3 \times 10^{-8}$ | 116 |
| 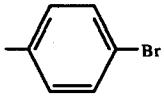 | H | OH | $3.3 \times 10^{-8}$ | 151 |
| 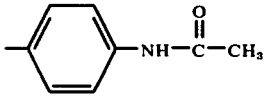 | H | OH | $8.9 \times 10^{-8}$ | 56 |
| 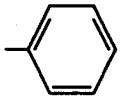 | H | OH | $3.8 \times 10^{-8}$ | 131 |
| 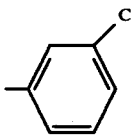 | H | OH | $2.5 \times 10^{-8}$ | 200 |
| 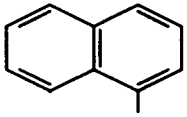 | H | OH | $2.9 \times 10^{-8}$ | 172 |
| 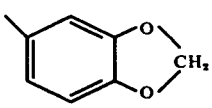 | H | OH | $4.3 \times 10^{-8}$ | 116 |
| 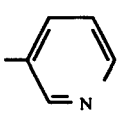 | H | OH | $2.5 \times 10^{-7}$ | 20 |
| 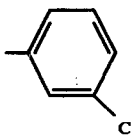 | H | H | $1.0 \times 10^{-7}$ | 50 |
| 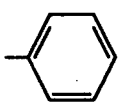 | H | H | $1.5 \times 10^{-7}$ | 33 |
| Allopurinol | | | $5 \times 10^{-6}$ | 1 |

It will be appreciated from the foregoing data that all of the compounds of this invention demonstrated activity at least twenty times greater than the commercial product, allopurinol. Indeed, Compounds (2), (3), (5), (6), (7) and (8) exhibited activity ranging between 100 and 200 times greater than allopurinol. It should also be noted that the compounds of the present invention also possess acceptable toxicity levels, $LD_{50}$, generally on the order of approximately 200 milligrams per kilogram of body weight.

The xanthine oxidase inhibitors are administered as oral preparations, in capsule or tablet form. The tablets or capsules will contain from about 0.5 to about 50 milligrams of the inhibitor per tablet or capsule. The required dose of the inhibitor, of course, will vary depending upon the condition of the patient, but will normally range from approximately 10 to 200 milligrams per day. To inhibit effectively the enzyme xanthine oxidase, a concentration in the blood of approximately 1 to about 500 micrograms of the inhibitor per milliliter is required, preferably from 1 to about 50 micrograms per milliliter.

We claim:

1. A process for the inhibition of the enzyme xanthine oxidase comprising administering to a patient an oral preparation containing as its active ingredient a compound of the structure

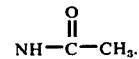

wherein R is phenyl, m-methylphenyl, p-methylphenyl, p-halophenyl, p-acetamidophenyl, 3,4-methylenedioxyphenyl, α-naphthyl, or 3-pyridyl; $R_1$ is H or an alkali metal or ammonium, and $R_2$ is H or $OR_1$ in a total daily dose of approximately 10 to 200 milligrams of the compound.

2. The process of claim 1 in which R is phenyl.

3. The process of claim 1 in which R is

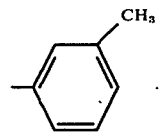

4. The process of claim 1 in which R is

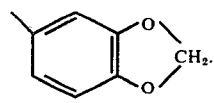

5. The process of claim 1 in which R is

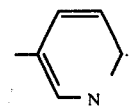

6. The process of claim 1 in which R is

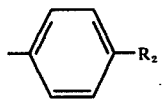

in which $R_2$ is methyl, a halogen, or $$NH-\overset{O}{\underset{\|}{C}}-CH_3.$$

* * * * *